US012582380B2

(12) United States Patent
Suwa

(10) Patent No.: US 12,582,380 B2
(45) Date of Patent: Mar. 24, 2026

(54) ENDOSCOPE AND DISTAL END BODY

(71) Applicant: OLYMPUS MEDICAL SYSTEMS CORP., Tokyo (JP)

(72) Inventor: Takahiro Suwa, Hachioji (JP)

(73) Assignee: OLYMPUS MEDICAL SYSTEMS CORP., Tokyo (JP)

( * ) Notice: Subject to any disclaimer, the term of this patent is extended or adjusted under 35 U.S.C. 154(b) by 36 days.

(21) Appl. No.: 18/651,839

(22) Filed: May 1, 2024

(65) Prior Publication Data

US 2024/0277314 A1      Aug. 22, 2024

Related U.S. Application Data

(63) Continuation of application No. PCT/JP2022/004327, filed on Feb. 3, 2022.

(51) Int. Cl.
*A61B 8/12* (2006.01)
*A61B 1/06* (2006.01)
*A61B 8/00* (2006.01)

(52) U.S. Cl.
CPC ................ *A61B 8/12* (2013.01); *A61B 8/445* (2013.01); *A61B 1/0676* (2013.01)

(58) Field of Classification Search
None
See application file for complete search history.

(56) References Cited

U.S. PATENT DOCUMENTS

| | | | |
|---|---|---|---|
| 2004/0082836 A1 | 4/2004 | Hino | |
| 2015/0265142 A1 | 9/2015 | Ogawa | |
| 2016/0367114 A1 * | 12/2016 | Iizuka | ................ A61B 1/00096 |

FOREIGN PATENT DOCUMENTS

| | | | | |
|---|---|---|---|---|
| JP | 2001269342 A | * | 10/2001 | |
| JP | 2004141316 A | | 5/2004 | |
| JP | 2018171256 A | | 11/2018 | |
| WO | 2014208218 A1 | | 12/2014 | |
| WO | 2016021231 A1 | | 2/2016 | |

OTHER PUBLICATIONS

English translation of JP-2001269342; Itou Keiji; Feb. 10, 2001.*
International Search Report dated Apr. 19, 2022 issued in PCT/JP2022/004327.

* cited by examiner

*Primary Examiner* — Shahdeep Mohammed
(74) *Attorney, Agent, or Firm* — Scully, Scott, Murphy & Presser, P.C.

(57) ABSTRACT

An endoscope includes: a distal end body positioned at a distal end of an insertion portion; and a first built-in component and a second built-in component each having a distal end portion housed in the distal end body. The distal end body includes: a first housing portion that extends along a first direction and houses the distal end portion of the first built-in component; a first opening portion communicating with the first housing portion and being open in at least a second direction; a second housing portion that communicates with the first housing portion, extends along the first direction at a position shifted in a third direction, and houses the distal end portion of the second built-in component; and a second opening portion communicating with the second housing portion and be open in at least the second direction.

19 Claims, 11 Drawing Sheets

ENDOSCOPE AND DISTAL END BODY

CROSS-REFERENCE TO RELATED APPLICATION

This application is a continuation of International Application No. PCT/JP2022/004327, filed on Feb. 3, 2022, the entire contents of which are incorporated herein by reference.

BACKGROUND

1. Technical Field

The present disclosure relates to an endoscope and a distal end body.

2. Related Art

In the related art, an endoscope includes an imaging part that captures images of the interior of a subject and an illumination part that irradiates the interior of the subject with illumination light. The imaging part and the illumination part are housed in a distal end body at a distal end of an insertion portion configured to be inserted into the subject.

An endoscope having an imaging part and an illumination part arranged one above the other in a distal end body is described in Japanese Patent Application Laid-open No. 2018-171256. Arranging the imaging part and the illumination part one above the other eliminates the need for a wall to be provided between a space for housing the imaging part and a space for housing the illumination part and thus enables the distal end body to be reduced in diameter.

SUMMARY

In some embodiments, an endoscope includes: a distal end body that is positioned at a distal end of an insertion portion configured to be inserted into a subject; and a first built-in component and a second built-in component each having a distal end portion housed in the distal end body. The distal end body includes: a first housing portion that extends along a first direction along a longitudinal direction of the distal end body and houses the distal end portion of the first built-in component; a first opening portion in which the distal end portion of the first built-in component is fitted, the first opening portion communicating with the first housing portion and being open in at least a second direction; a second housing portion that communicates with the first housing portion, extends along the first direction at a position shifted in a third direction orthogonal to both the first direction and the second direction, and houses the distal end portion of the second built-in component; and a second opening portion in which the distal end portion of the second built-in component is fitted, the second opening portion communicating with the second housing portion and be open in at least the second direction, and the second direction is a direction orthogonal to the first direction.

In some embodiments, provided is a distal end body positioned at a distal end of an insertion portion of an endoscope to be inserted into a subject. The distal end body includes: a first housing portion that extends along a first direction along a longitudinal direction of the distal end body and houses a distal end portion of a first built-in component; a first opening portion in which the distal end portion of the first built-in component is fitted, the first opening portion communicating with the first housing portion and be open in at least a second direction; a second housing portion that communicates with the first housing portion, extends along the first direction at a position shifted in a third direction orthogonal to both the first direction and the second direction, and houses a distal end portion of a second built-in component; and a second opening portion in which the distal end portion of the second built-in component is fitted, the second opening portion communicating with the second housing portion and be open in at least the second direction, and the second direction is a direction orthogonal to the first direction.

The above and other features, advantages and technical and industrial significance of this disclosure will be better understood by reading the following detailed description of presently preferred embodiments of the disclosure, when considered in connection with the accompanying drawings.

DETAILED DESCRIPTION

Embodiments of an endoscope and a distal end body, according to the disclosure, will hereinafter be described by reference to the drawings. The disclosure is not limited by these embodiments. With respect to the following embodiments, oblique-viewing endoscopes and their distal end bodies are described as examples, but the disclosure is generally applicable to oblique-viewing and side-viewing endoscopes and their distal end bodies.

Furthermore, any elements that are the same or corresponding to each other are assigned with the same reference sign throughout the drawings, as appropriate. It also needs to be noted that the drawings are schematic, and relations between dimensions of each element therein and proportions between the elements therein may be different from the actual ones. The drawings may also include a portion that differs in its dimensional relations or proportions between the drawings.

Embodiments

Configuration of Endoscope System

Figure 1:
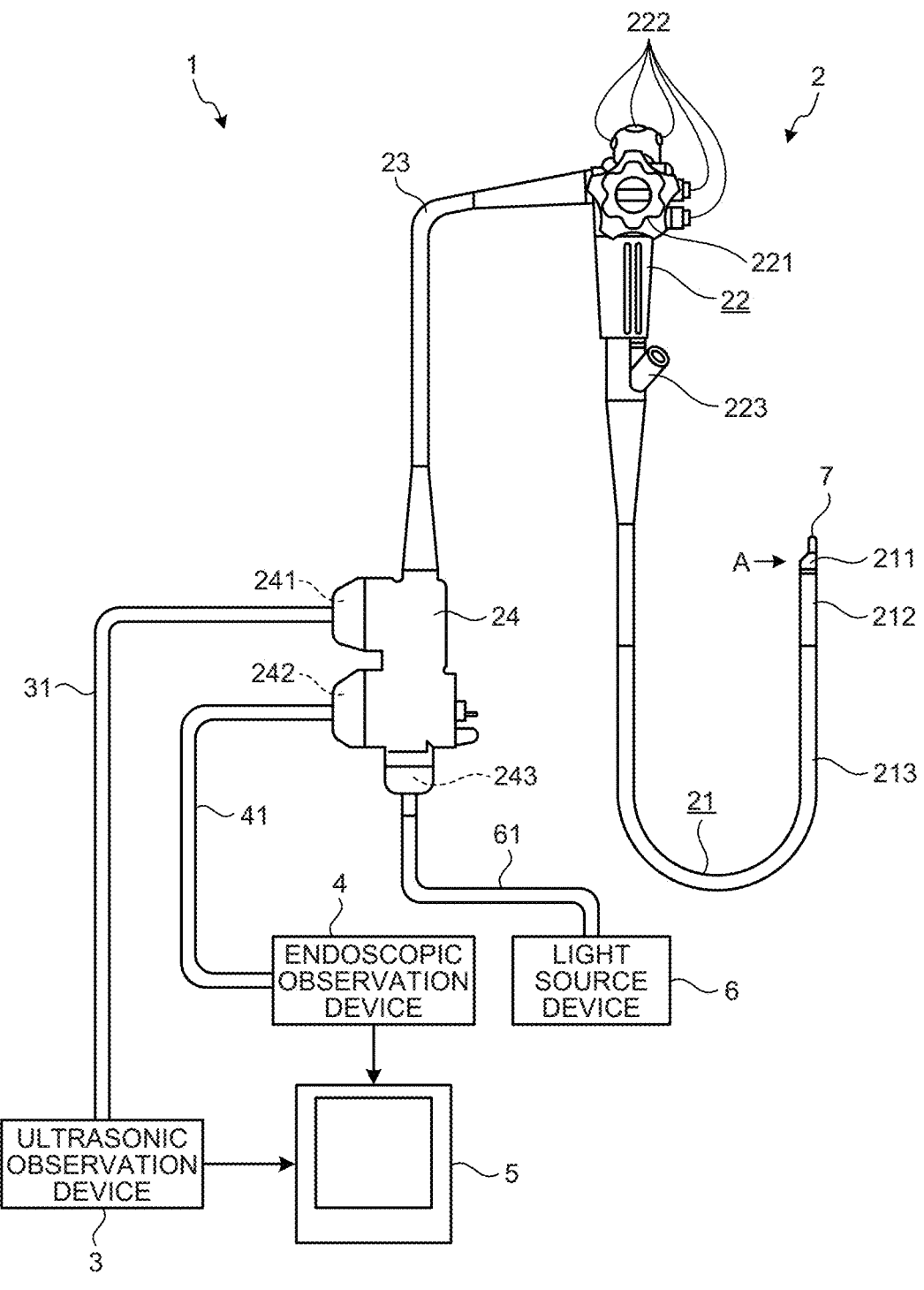
FIG. 1 is a diagram schematically illustrating an endoscope system according to an embodiment.

FIG. 1 is a diagram schematically illustrating an endoscope system according to an embodiment. An endoscope system 1 is a system for ultrasound diagnosis of the interior of a subject, such as a human, by use of an ultrasound endoscope. This endoscope system 1 includes, as illustrated in FIG. 1, an ultrasound endoscope 2, an ultrasonic observation device 3, an endoscopic observation device 4, a display device 5, and a light source device 6.

The ultrasound endoscope 2 includes an ultrasound transducer provided at a distal end portion of the ultrasound endoscope 2. This ultrasound transducer converts an electric pulse signal received from the ultrasonic observation device 3 into ultrasound pulses and emits the ultrasound pulses to the subject, converts ultrasound echoes reflected in the subject into an electric echo signal representing the reflected ultrasound echoes as change in voltage, and outputs the electric echo signal.

The ultrasound endoscope 2 includes an imaging optical system and an imaging element and is capable of being inserted into the digestive tract (esophagus, stomach, duodenum, and large intestine) or the respiratory organs (trachea and bronchi) of the subject and imaging the digestive tract or the respiratory organs. Furthermore, by using ultrasound, the ultrasound endoscope 2 is capable of imaging organs surrounding the gastrointestinal tract or respiratory organs (such as the pancreas, cholecystis, biliary duct, biliary tract, lymph nodes, mediastinal organs, and/or blood vessels) by using ultrasound. The ultrasound endoscope 2 also includes a light guide that guides illumination light to be emitted to the subject upon optical imaging. This light guide includes a distal end portion that reaches a distal end of an insertion portion configured to be inserted into the subject of the ultrasound endoscope 2, and a proximal end portion connected to the light source device 6 that generates illumination light.

The ultrasound endoscope 2 includes, as illustrated in FIG. 1, an insertion portion 21, an operating portion 22, a universal cord 23, and a connector 24.

The insertion portion 21 is a part to be inserted into the subject. This insertion portion 21 includes, as illustrated in FIG. 1: a distal end body 211 that is provided near a distal end of the ultrasound endoscope 2, holds a convex ultrasound transducer 7, and is rigid; a bending tube 212 that bends in a bending direction orthogonal to a central axis thereof; and an insertion tube 213 having a central axis. The distal end body 211 is provided at a distal end of the bending tube 212, the bending tube 212 is provided at a distal end of the insertion tube 213, and the insertion tube 213 is provided at a distal end of the operating portion 22. A configuration of a distal end of the insertion portion 21 and a configuration of the bending tube 212 will be described later.

The operating portion 22 is a part that is connected to a proximal end of the insertion portion 21 and receives various kinds of operation from an operator, such as a medical doctor. This operating portion 22 includes, as illustrated in FIG. 1, a bending knob 221 that receives bending operation for bending the bending tube 212, and plural operating members 222 for performing various kinds of operation. Furthermore, the operating portion 22 includes a treatment tool insertion opening 223 formed therein, the treatment tool insertion opening 223 communicating with a treatment tool insertion passage and being for inserting a treatment tool into the treatment tool insertion passage.

The universal cord 23 is a cable that extends from the operating portion 22 and includes, arranged therein, for example, plural signal cables that transmit various signals and an optical fiber that transmits illumination light supplied from the light source device 6.

The connector 24 is provided at a distal end of the universal cord 23. The connector 24 includes a first connector portion 241 where an ultrasound cable 31 is connected, a second connector portion 242 where a video cable 41 is connected, and a third connector portion 243 where an optical fiber cable 61 is connected.

The ultrasonic observation device 3 is electrically connected to the ultrasound endoscope 2 via the ultrasound cable 31 (see FIG. 1), outputs a pulse signal to the ultrasound endoscope 2 via the ultrasound cable 31, and receives an echo signal from the ultrasound endoscope 2 via the ultrasound cable 31. The ultrasonic observation device 3 generates an ultrasound image by subjecting the echo signal to predetermined processing.

The endoscopic observation device 4 is electrically connected to the ultrasound endoscope 2 via the video cable 41 (see FIG. 1) and receives an image signal from the ultrasound endoscope 2 via the video cable 41. The endoscopic observation device 4 then generates an endoscopic image by subjecting the image signal to predetermined processing.

The display device 5 is formed by use of, for example, liquid crystal or organic electroluminescence (EL), a projector, or a cathode ray tube (CRT), and displays, for example, an ultrasound image generated in the ultrasonic observation device 3 or an endoscopic image generated in the endoscopic observation device 4.

The light source device 6 is connected to the ultrasound endoscope 2 via the optical fiber cable 61 (see FIG. 1) and supplies, via the optical fiber cable 61, illumination light for illuminating the interior of the subject, to the ultrasound endoscope 2.

Configuration at Distal End of Insertion Portion

Figure 2:
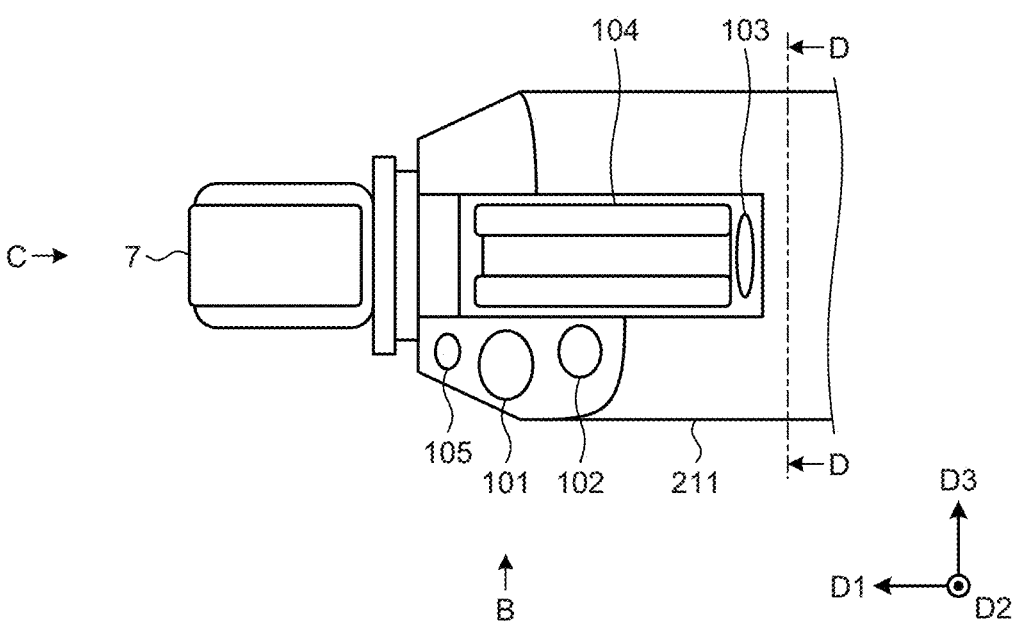
FIG. 2 is a view from a direction of A in FIG. 1.
Figure 3:
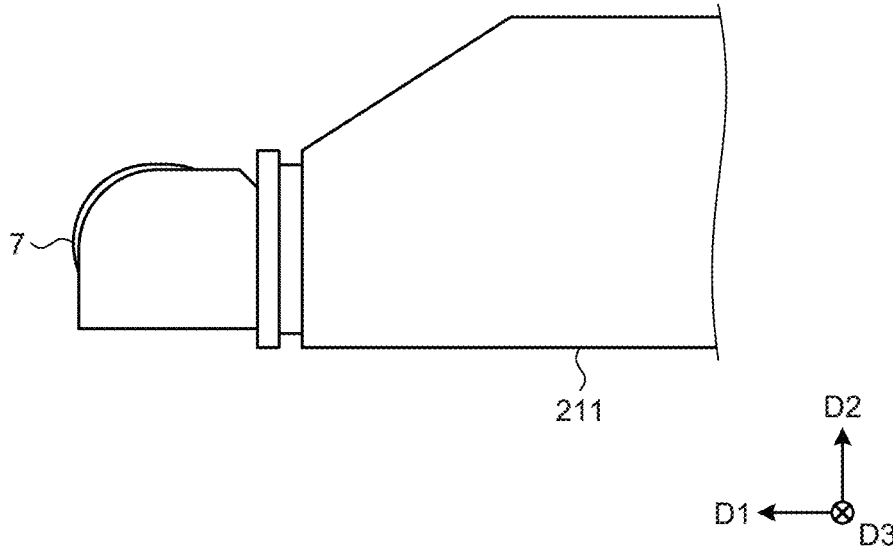
FIG. 3 is a view from a direction of B in FIG. 2.
Figure 4:
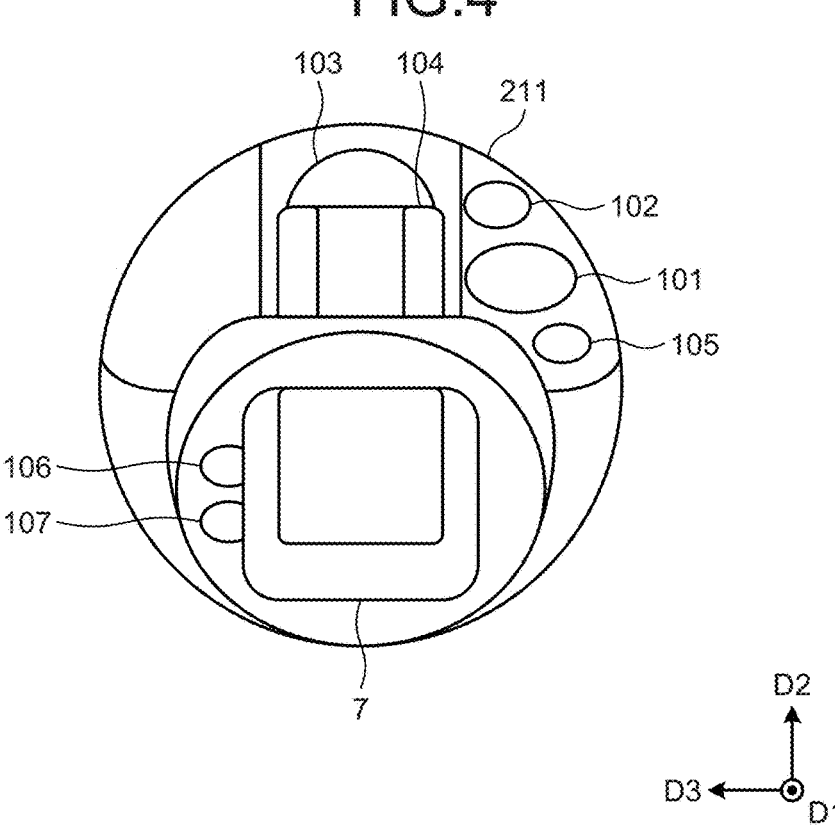
FIG. 4 is a view from a direction of C in FIG. 2.

FIG. 2 is a view from a direction of A in FIG. 1. FIG. 3 is a view from a direction of B in FIG. 2. FIG. 4 is a view from a direction of C in FIG. 2. A direction along a longitudinal direction of the distal end body 211 will hereinafter be referred to as a first direction D1, a direction orthogonal to the first direction as a second direction D2, and a direction orthogonal to both the first direction D1 and second direction D2 as a third direction D3.

As illustrated in FIG. 2 to FIG. 4, the distal end body 211 positioned at the distal end of the insertion portion 21 includes, arranged therein, an imaging lens 101 configured to condense light from the subject, an illumination lens 102 configured to illuminate the interior of the subject with illumination light, a treatment tool protrusion opening 103 from which a treatment tool such as forceps is caused to protrude, a treatment tool raising stand 104 configured to raise the treatment tool in the second direction D2, a gas feeding and water feeding opening 105 configured to release gas such as air or liquid such as water, a balloon water feeding opening 106 configured to send out liquid such as water into a balloon, and a balloon suction opening 107 where liquid, such as water, is sucked from the inside of the balloon.

Configuration Inside Distal End Body

Figure 5:
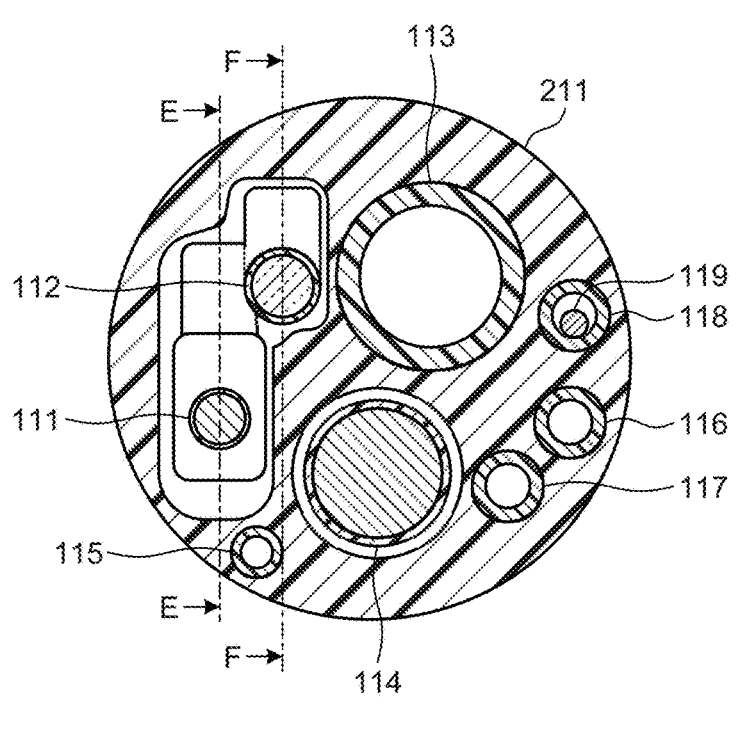
FIG. 5 is a sectional view illustrating a configuration inside a distal end body.
Figure 5:
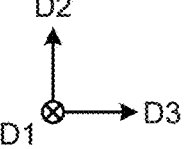

FIG. 5 is a sectional view illustrating a configuration inside a distal end body. As illustrated in FIG. 5, the distal end body 211 includes, inserted therein, a signal cable 111 configured to transmit an image signal converted from light received by the imaging lens 101, a light guide 112 configured to transmit illumination light to the illumination lens 102, a channel tube 113 into which the treatment tool is inserted, a transducer cable 114 configured to transmit and receive signals to and from the ultrasound transducer 7, a gas feeding and water feeding tube 115 configured to feed gas or liquid to the gas feeding and water feeding opening 105, a balloon water feeding tube 116 configured to feed liquid to the balloon water feeding opening 106, a balloon suction tube 117 configured to transmit liquid sucked from the balloon suction opening 107, a treatment tool raising tube 118 into which a treatment tool raising wire 119 is inserted, and the treatment tool raising wire 119 configured to raise the treatment tool raising stand 104 in response to operation of the operating portion 22.

Configuration of Imaging Part

Figure 6:
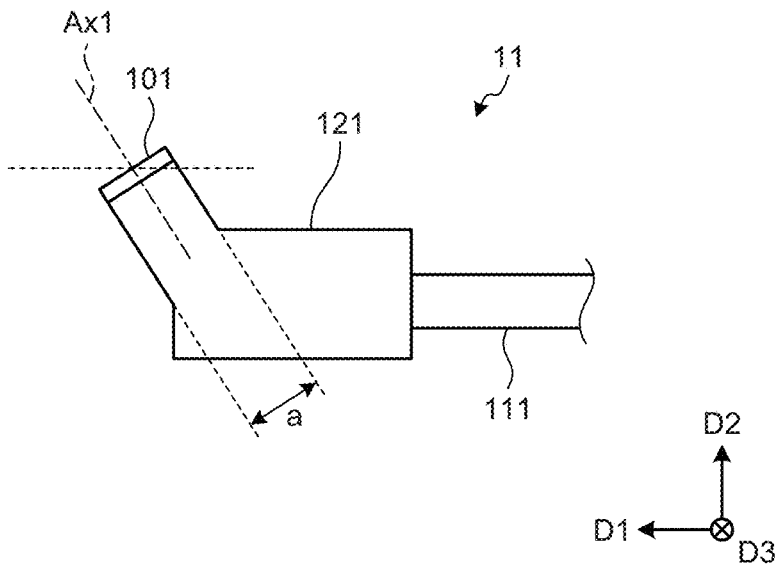
FIG. 6 is a diagram illustrating a configuration of an imaging part.

FIG. 6 is a diagram illustrating a configuration of an imaging part. As illustrated in FIG. 6, an imaging part 11 that is a first built-in component includes the imaging lens 101 positioned at a distal end of the imaging part 11, an imaging unit 121 including an imaging element that converts light condensed by the imaging lens 101 into an image signal, and the signal cable 111 that transmits the image signal generated by the imaging element to the endoscopic observation device 4. A distal end portion of the imaging part 11 is housed in the distal end body 211 and the imaging part 11 captures an image of the subject by converting light received from the outside of the distal end into an image signal. A reference symbol, "a", in FIG. 6 will be described later (see description of FIG. 14). The imaging unit 121 may include an optical element, such as a lens different from the imaging lens 101.

In the imaging part 11, an axis Ax1 direction near the distal end having the imaging lens 101 is oblique to a direction of extension of the signal cable 111. More specifically, a rear end portion of the imaging unit 121 is along the first direction D1 and a distal end portion of the imaging unit 121 extends in the first direction D1 and the second direction D2. In other words, the imaging unit 121 is formed to have an axis that bends in the middle.

Configuration of Illumination Part

Figure 7:
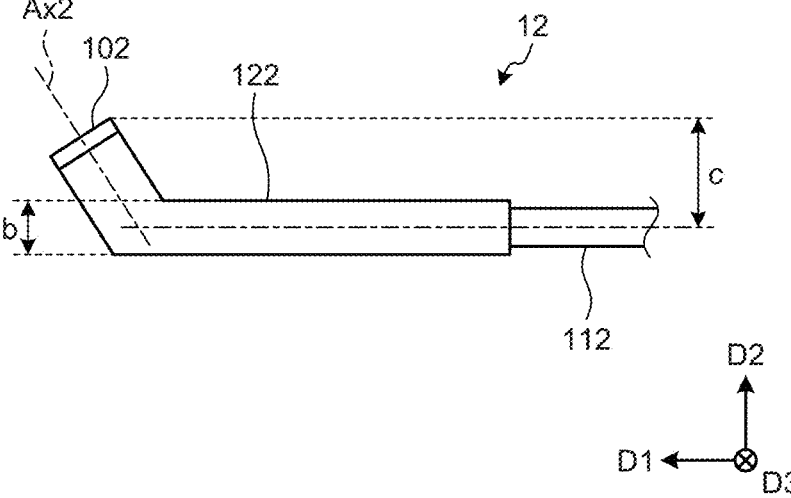
FIG. 7 is a diagram illustrating a configuration of an illumination part.

FIG. 7 is a diagram illustrating a configuration of an illumination part. As illustrated in FIG. 7, the illumination part 12 that is a second built-in component includes an illumination lens 102 positioned at a distal end of the illumination part 12, and an illumination unit 122 positioned at a proximal end of the illumination lens 102. The illumination unit 122 includes the light guide 112 that transmits illumination light from the light source device 6. The illumination part 12 includes a distal end portion housed in the distal end body 211 and emits illumination light to the outside near the distal end of the illumination part 12. Reference symbols, "b" and "c", in FIG. 7 will be described later (see description of FIG. 14). The illumination unit 122 may include a tube covering the light guide 112 or a metallic pipe. Furthermore, the illumination unit 122 may be an illumination unit not configured to include a light guide like the illumination unit 122. For example, this illumination unit may include a light emission diode (LED) and a leading wire connecting the LED and a power source to each other.

In the illumination part 12, an axis Ax2 direction near the distal end having the illumination lens 102 is oblique to a direction of extension of the light guide 112. More specifically, a rear end portion of the illumination unit 122 is along the first direction D1 and a distal end portion of the illumination unit 122 extends in the first direction D1 and the second direction D2. In other words, the illumination unit 122 is formed to have an axis that bends in the middle.

Configuration of Distal End Body

Figure 8:
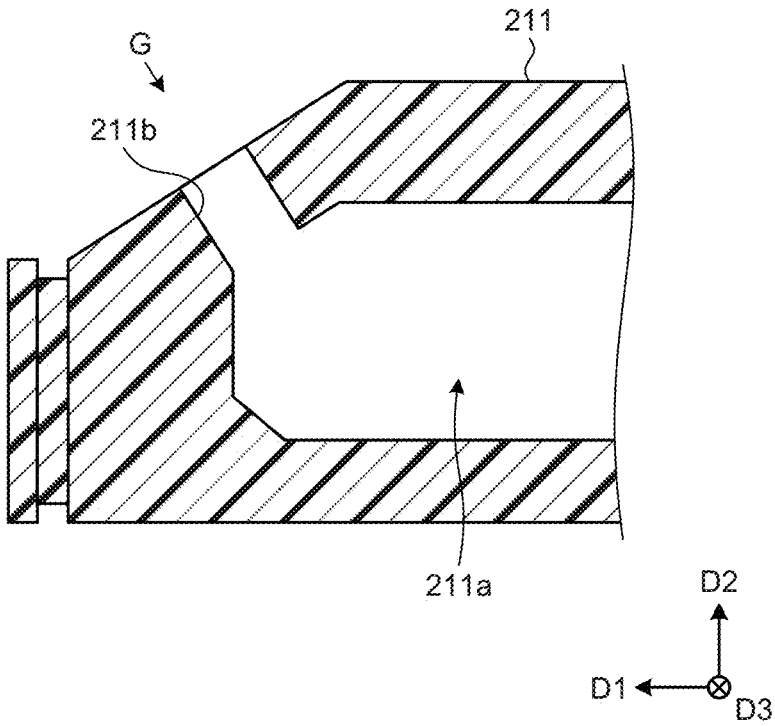
FIG. 8 is a sectional view corresponding to an E-E line in FIG. 5.

FIG. 8 is a sectional view corresponding to an E-E line in FIG. 5. As illustrated in FIG. 8, the distal end body 211 includes, formed therein, an imaging housing portion 211a that is a first housing portion and an imaging opening portion 211b that is a first opening portion.

The imaging housing portion 211a extends along the first direction D1 and houses the distal end portion of the imaging part 11.

The imaging opening portion 211b communicates with the imaging housing portion 211a and is open in the first direction D1 and the second direction D2. In other words, the imaging opening portion 211b is open in at least the second direction D2. Furthermore, the distal end portion of the imaging part 11 is fitted in the imaging opening portion 211b.

Figure 9:
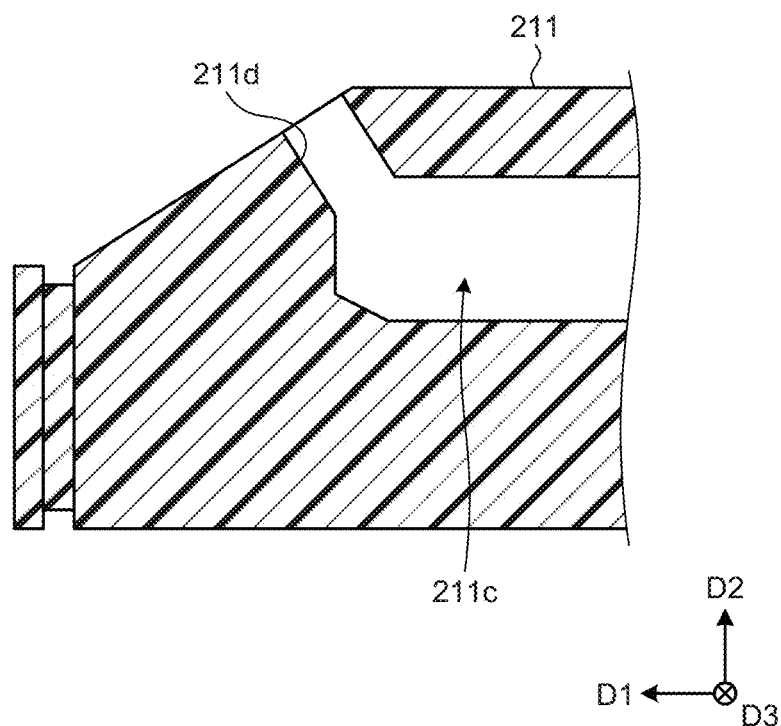
FIG. 9 is a sectional view corresponding to an F-F line in FIG. 5.

FIG. 9 is a sectional view corresponding to an F-F line in FIG. 5. As illustrated in FIG. 9, the distal end body 211 includes, formed therein, an illumination housing portion 211c that is a second housing portion and an illumination opening portion 211d that is a second opening portion.

The illumination housing portion 211c communicates with the imaging housing portion 211a, extends along the first direction D1, and houses the distal end portion of the illumination part 12.

The illumination opening portion 211d communicates with the illumination housing portion 211c and is open in the first direction D1 and the second direction D2. In other words, the illumination opening portion 211d is open in at least the second direction D2. Furthermore, the distal end portion of the illumination part 12 is fitted in the illumination opening portion 211d.

Figure 10:
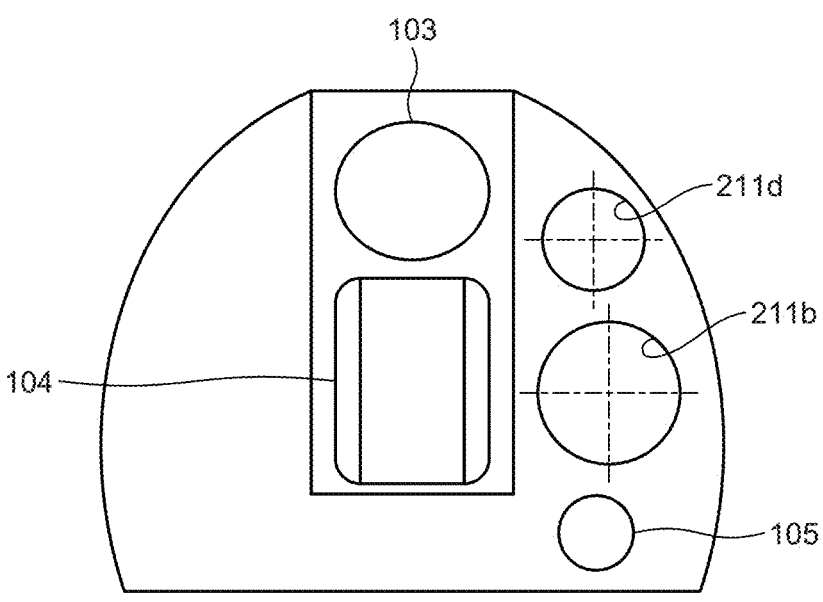
FIG. 10 is a diagram illustrating part of a view from a direction of G in FIG. 8.

FIG. 10 is a diagram illustrating part of a view from a direction of G in FIG. 8. As illustrated in FIG. 10, the imaging opening portion 211b is formed on a distal end side of the distal end body 211 with respect to the illumination opening portion 211d and is separate from the illumination opening portion 211d.

Figure 11:
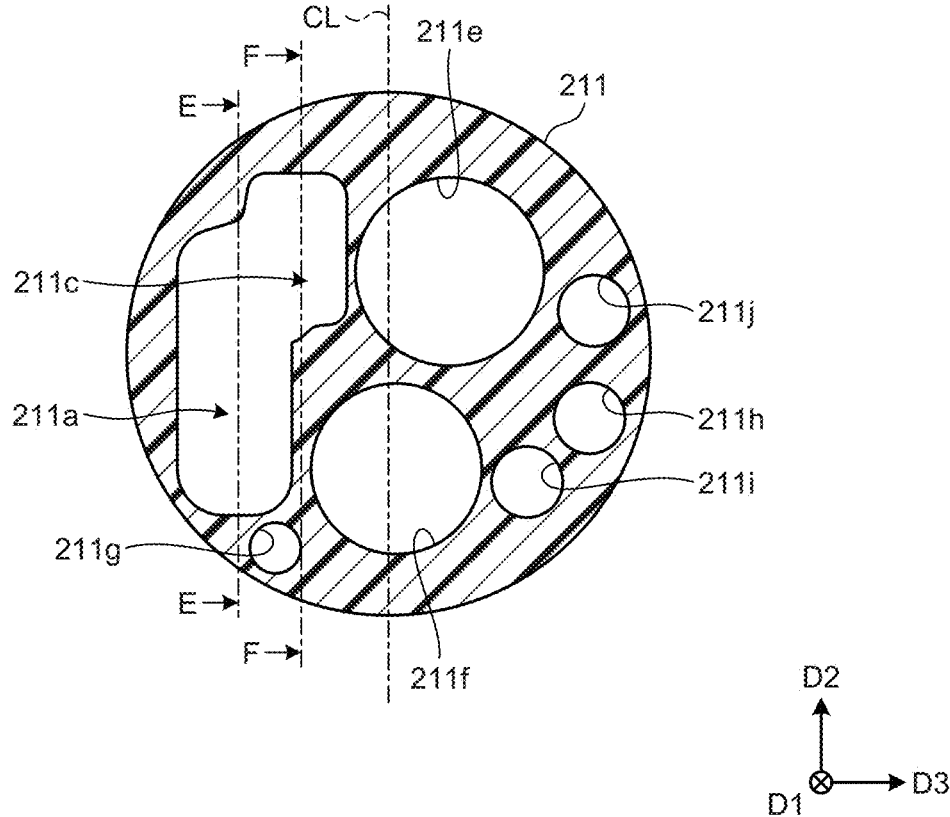
FIG. 11 is a sectional view of the distal end body corresponding to a D-D line in FIG. 2.

FIG. 11 is a sectional view of the distal end body corresponding to a D-D line in FIG. 2. As illustrated in FIG. 11, the illumination opening portion 211d extends along the first direction D1 at a position shifted in the third direction D3.

Furthermore, the distal end body 211 includes, formed therein: a treatment tool insertion channel 211e extending along the first direction D1, the treatment tool insertion channel 211e being where the channel tube 113 is arranged, the channel tube 113 being where the treatment tool is inserted; a transducer cable insertion channel 211f where the transducer cable 114 is arranged; a gas feeding and water feeding channel 211g where the gas feeding and water feeding tube 115 is arranged; a balloon water feeding channel 211h where the balloon water feeding tube 116 is arranged; a balloon suction channel 211i where the balloon suction tube 117 is arranged; and a treatment tool raising channel 211*j* where the treatment tool raising tube 118 and the treatment tool raising wire 119 are arranged.

Specifically, the treatment tool insertion channel 211*e* and the transducer cable insertion channel 211*f* are arranged in the third direction D3 and near a center line CL along the second direction D2. The treatment tool insertion channel 211*e* and the transducer cable insertion channel 211*f* are arranged one above the other along the second direction D2. Furthermore, the illumination housing portion 211*c* and the treatment tool raising channel 211*j* have been formed to have the treatment tool insertion channel 211*e* interposed therebetween. As described later, the imaging housing portion 211*a* and the illumination housing portion 211*c* communicate with each other. The gas feeding and water feeding channel 211*g* is formed in a lower region that is on one side of the treatment tool insertion channel 211*e* in the third direction D3, the one side being a side where the illumination housing portion 211*c* is arranged. Furthermore, the balloon water feeding channel 211*h* and the balloon suction channel 211*i* are formed in a lower region in relation to the second direction D2, like the transducer cable insertion channel 211*f*.

Attachment and Detachment of Imaging Part and Illumination Part

Figure 12:
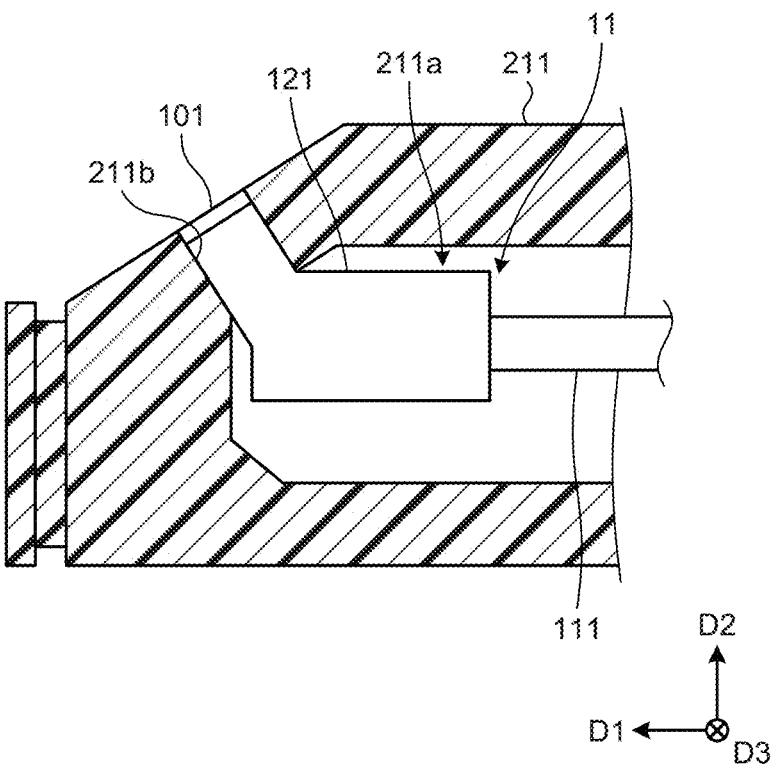
FIG. 12 is a diagram illustrating how the imaging part is attached and detached.
Figure 13:
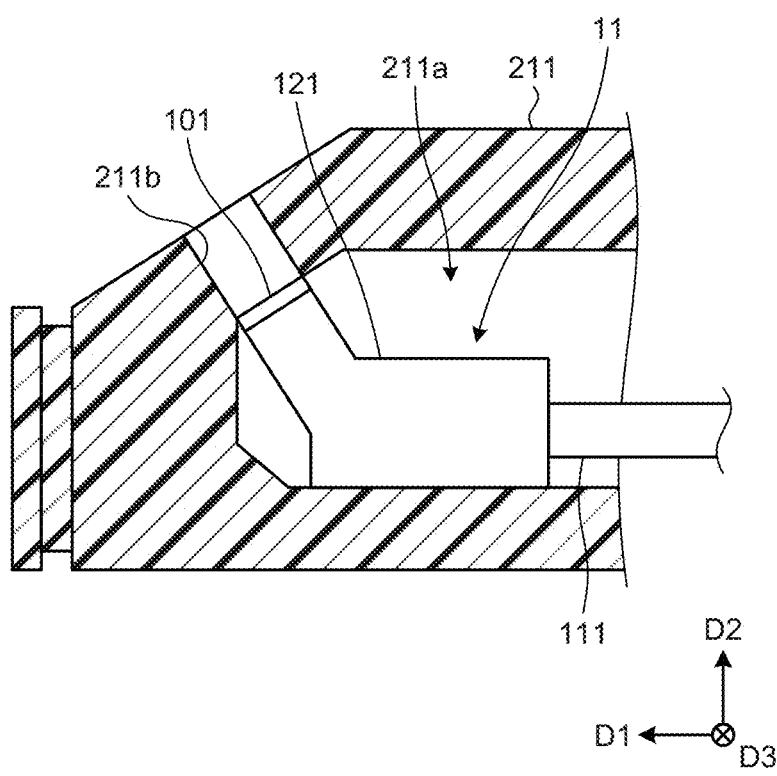
FIG. 13 is a diagram illustrating how the imaging part is attached and detached.

FIG. 12 and FIG. 13 are diagrams illustrating how the imaging part is attached and detached. To attach and detach the imaging part 11, the distal end portion of the imaging part 11 may be slid along the second direction D2 so that the imaging part 11 illustrated in FIG. 12 is brought into a state illustrated in FIG. 13 where the imaging part 11 has been removed, from a state illustrated in FIG. 12 where the imaging part 11 has been fitted in the imaging opening portion 211*b* of the distal end body 211.

Figure 14:
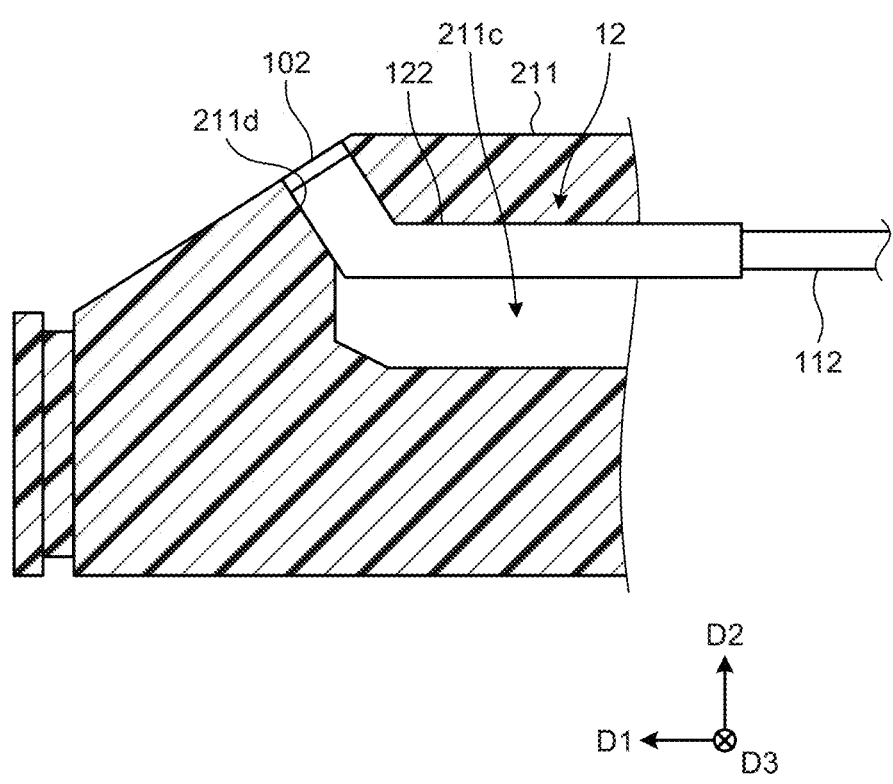
FIG. 14 is a diagram illustrating how the illumination part is attached and detached.
Figure 15:
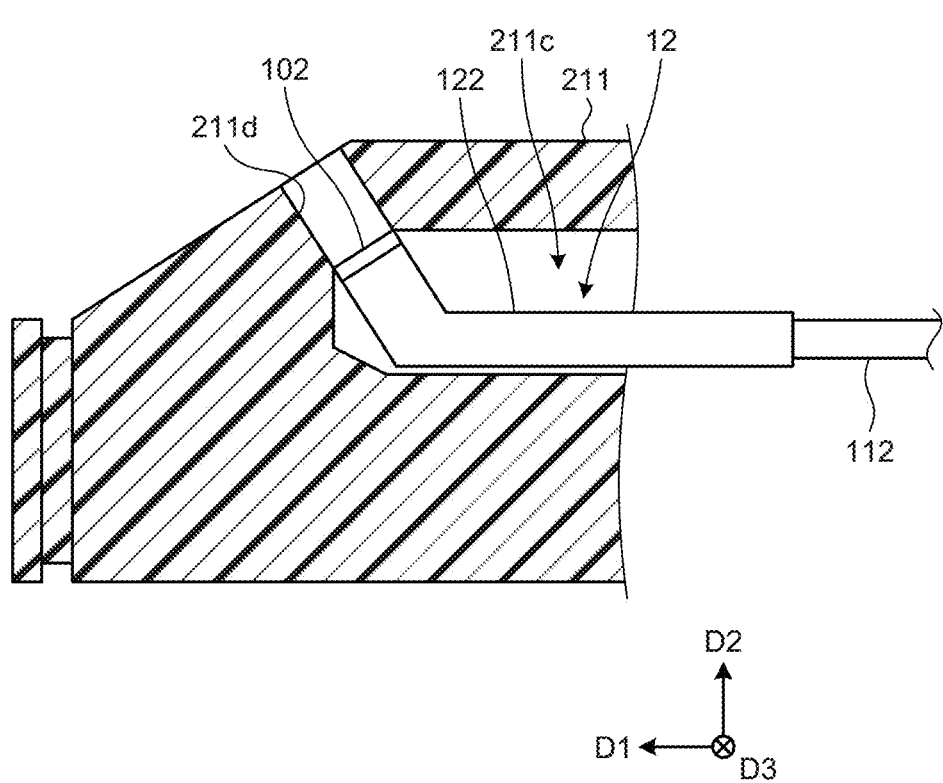
FIG. 15 is a diagram illustrating how the illumination part is attached and detached.

FIG. 14 and FIG. 15 are diagrams illustrating how the illumination part is attached and detached. To attach and detach the illumination part 12, the distal end portion of the illumination part 12 may be slid along the second direction D2 so that the illumination part 12 is brought into a state illustrated in FIG. 15 where the illumination part 12 has been removed, from a state illustrated in FIG. 14 where the illumination part 12 has been fitted in the illumination opening portion 211*d* of the distal end body 211.

Figure 16:
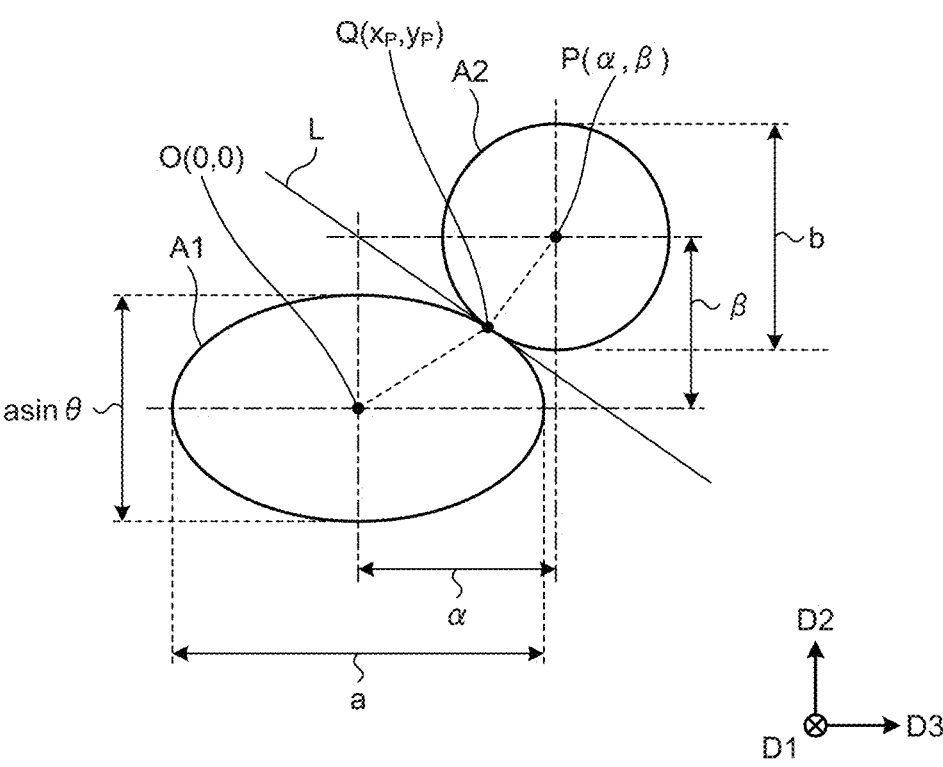
FIG. 16 is a diagram illustrating a positional relation between the imaging part and the illumination part.
Figure 17:
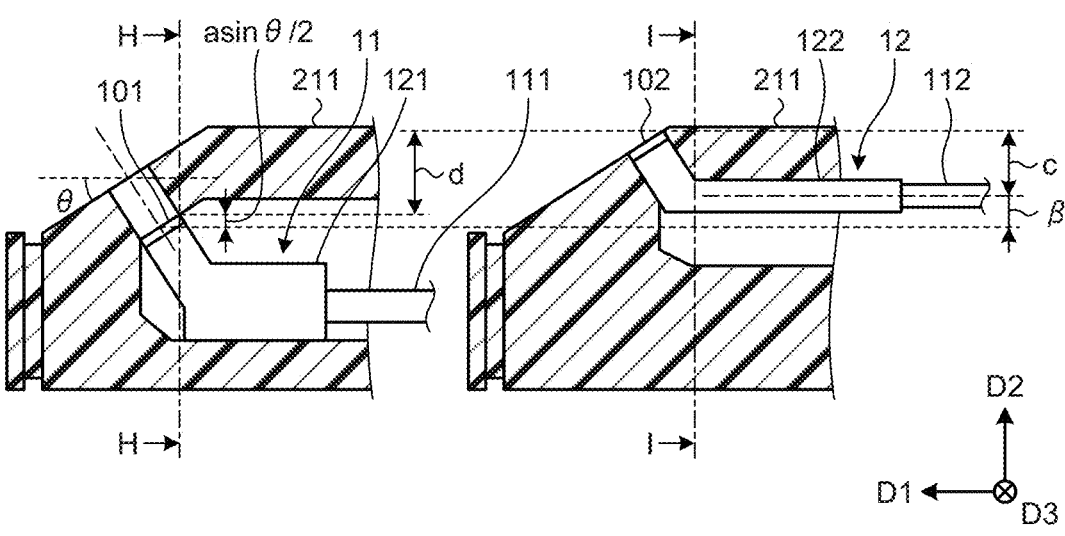
FIG. 17 is a diagram illustrating the positional relation between the imaging part and the illumination part.

Positional Relation Between Imaging Housing Portion and Illumination Housing Portion FIG. 16 and FIG. 17 are diagrams illustrating a positional relation between the imaging part and the illumination part. FIG. 16 illustrates the positional relation along a direction orthogonal to the first direction D1. FIG. 17 illustrates the positional relation along the first direction D1. An ellipse A1 in FIG. 16 represents a region where the imaging lens 101 passes in a plane orthogonal to the first direction D1 when the imaging part 11 is attached and detached and is a shape as viewed from a proximal end of the imaging lens 101 in FIG. 17. Furthermore, a circle A2 in FIG. 16 represents a cross section of the illumination unit 122 in the plane orthogonal to the first direction D1 and is a shape as viewed from a proximal end of the illumination unit 122 in FIG. 17. In other words, the ellipse A1 in FIG. 16 is a diagram resulting from projection of the imaging lens 101 onto an H-H line cross section in FIG. 17, the imaging lens 101 being viewed from the proximal end. The circle A2 in FIG. 16 is a sectional view of the illumination unit 122 taken on an I-I line in FIG. 17, the illumination unit 122 being viewed from the proximal end. Any layout where the ellipse A1 and the circle A2 do not overlap each other enables the imaging part 11 to be individually attached to and detached from distal end body 211 in a state where the illumination part 12 has been installed in the distal end body 211. Conditions for the ellipse A1 and the circle A2 to be in contact with each other will be described hereinafter.

In FIG. 16, the reference numeral, "α", is the diameter of the imaging lens 101. The reference numeral, "b", is the diameter of the illumination unit 122. A reference numeral, "α", represents a distance between the imaging part 11 and the illumination part 12 along the third direction D3. A reference numeral, "β", represents a distance between the imaging part 11 and the illumination part 12 along the second direction D2. The center of the ellipse A1 is assumed to be at a point O (0,0), the center of the circle A2 is assumed to be at a point P (α, β), and the point of contact between the ellipse A1 and the circle A2 is assumed to be at a point Q ($x_p$, $y_p$). In FIG. 17, the reference numeral, "c", represents a distance in the D2 direction from an upper end of the illumination lens 102 to the center of the light guide 112. A reference numeral, "d", represents a distance in the D2 direction from the upper end of the illumination lens 102 to an upper end of the imaging lens 101. A reference numeral, "θ", represents an angle formed between the first direction D1 and a distal end surface of the imaging lens 101.

As illustrated in FIG. 16, the point Q positioned on the ellipse A1 is a point on an ellipse and thus satisfies the following Equation (1).

$$\left(\frac{x_p}{\alpha/2}\right)^2 + \left(\frac{y_p}{\alpha \sin \theta/2}\right)^2 = 1 \tag{1}$$

Furthermore, the point Q positioned on the circle A2 is also a point on a circle having its center at the point P and thus satisfies the following Equation (2).

$$(x_p - \alpha)^2 + (y_p - \beta)^2 = \left(\frac{b}{2}\right)^2 \tag{2}$$

Furthermore, for the ellipse A1 and the circle A2 to contact each other at the point Q, a tangent to the ellipse A1 at the point Q and a tangent to the circle A2 at the point Q must be on the same straight line L. Therefore, the tangent to the ellipse A1 at the point Q has a gradient equal to that of the tangent to the circle A2 at the point Q and the following Equation (3) holds.

$$-\frac{(\alpha \sin \theta/2)^2 \cdot x_p}{(\alpha/2)^2 \cdot y_p} = -\frac{(x_p - \alpha)}{(y_p - \beta)} \tag{3}$$

As illustrated in FIG. 17, the sum a sin θ/2+d of a sin θ/2 and d is equal to the sum c+β of c and β.

$$\alpha \sin \theta/2 + d = c + \beta \tag{4}$$

As a result, in a case where the distance along the third direction D3 between the imaging part 11 and the illumination part 12 is equal to or larger than α satisfying Equations (1) to (4) and the distance along the second direction D2 between the imaging part 11 and the illumination part 12 is equal to or larger than β satisfying Equations (1) to (4), the imaging part 11 is able to be individually attached to and detached from the distal end body 211. In other words, in a case where the distance along the third direction D3 between the central axis of the imaging housing portion 211*a* and the central axis of the illumination housing portion 211*c* is equal to or larger than α satisfying Equations (1) to (4) and the distance along the second direction D2 between the central axis of the imaging housing portion 211*a* and the central axis of the illumination housing portion 211*c* is equal to or larger than β satisfying Equations (1) to (4), the imaging part 11 is able to be individually attached to and detached from the distal end body 211. Furthermore, because there is no wall between the imaging part 11 and the illumination part 12 in this embodiment, the diameter of the distal end body 211 is small, and because the distal end body 211 does not have a lid, the distal end body 211 is not easily deteriorated over time.

Figure 18:
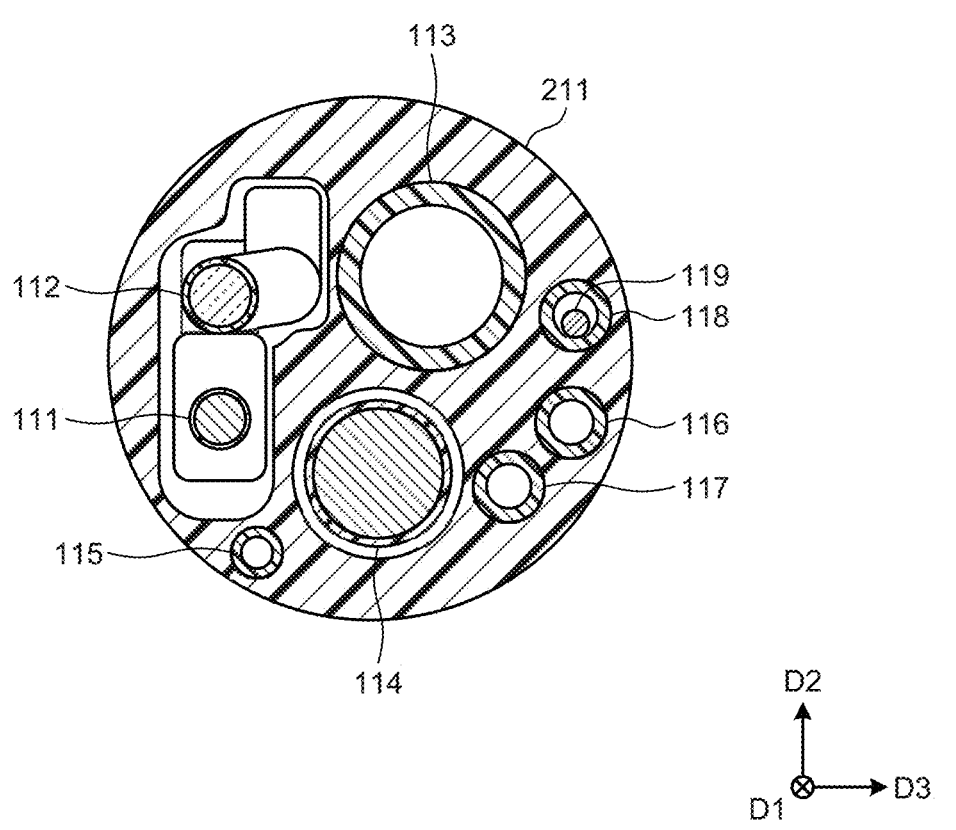
FIG. 18 is a sectional view illustrating a configuration inside the distal end body.

An example where the light guide 112 extends along the first direction D1 as illustrated in FIG. 5 has been described above with respect to the embodiment, but the embodiment is not limited to this example. FIG. 18 is a sectional view illustrating a configuration inside a distal end body. As illustrated in FIG. 18, rear ends of the signal cable 111 and the light guide 112 may extend along the first direction D1 at the same position along the third direction D3.

The imaging opening portion 211*b* and the illumination opening portion 211*d* have been described to be open in the first direction D1 and the second direction D2 but may be formed to be open only in the second direction D2.

First Modified Example

Figure 19:
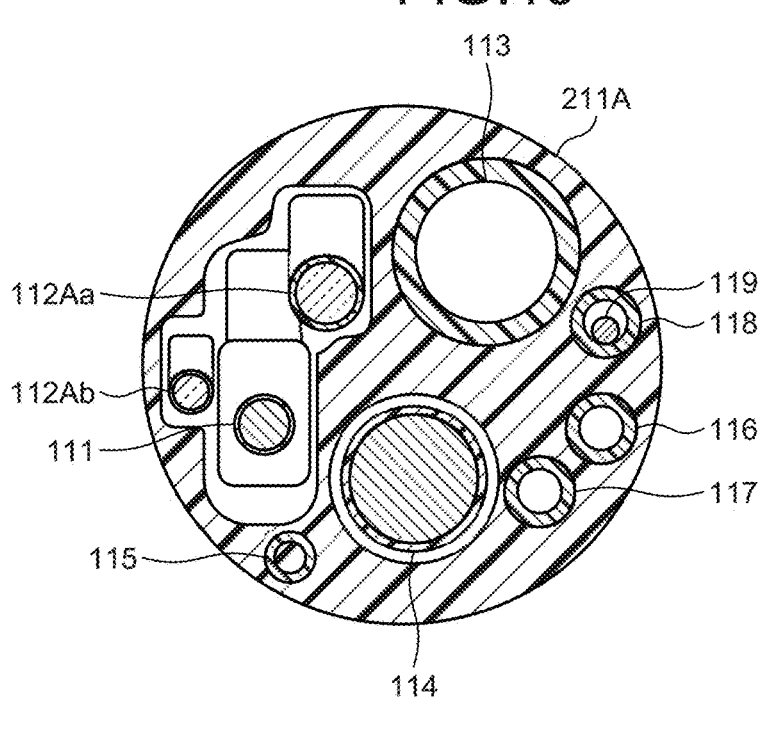
FIG. 19 is a sectional view illustrating a configuration inside a distal end body in an endoscope system according to a first modified example.
Figure 19:
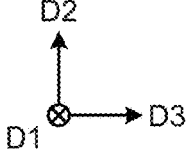

FIG. 19 is a sectional view illustrating a configuration inside a distal end body in an endoscope system according to a first modified example. As illustrated in FIG. 19, a housing portion that houses a signal cable 111 and two light guides 112Aa and 112Ab may be formed in a distal end body 211A. This configuration having the two light guides 112Aa and 112Ab also enables reduction in diameter of the distal end body 211A by having the two light guides 112Aa and 112Ab housed in the communicating housing portion.

Second Modified Example

Figure 20:
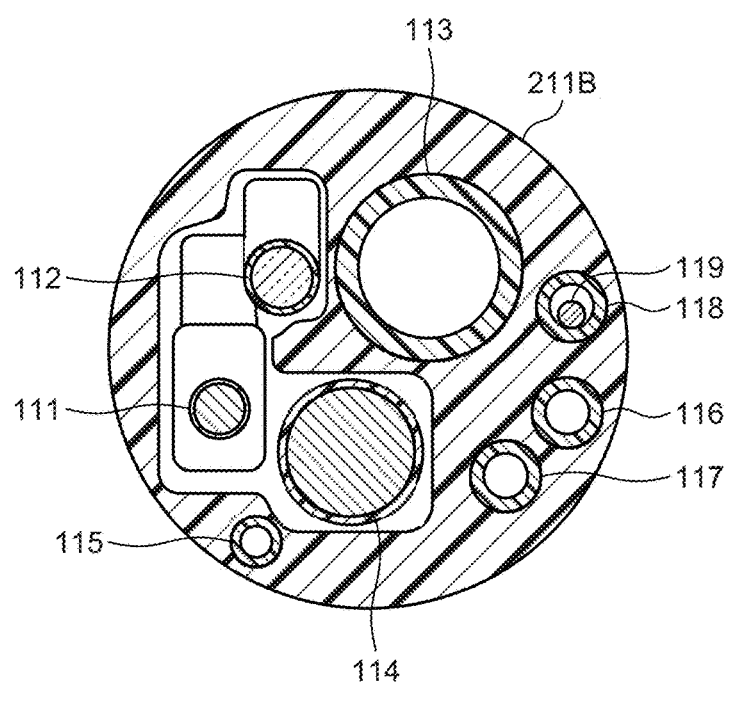
FIG. 20 is a sectional view illustrating a configuration inside a distal end body in an endoscope system according to a second modified example.
Figure 20:
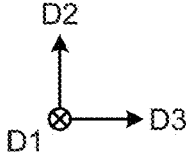

FIG. 20 is a sectional view illustrating a configuration inside a distal end body in an endoscope system according to a second modified example. As illustrated in FIG. 20, a housing portion that houses a signal cable 111, a light guide 112, and a transducer cable 114 may be formed in a distal end body 211B. A housing portion that houses distal end portions of three or more built-in components may be formed in a distal end body like this. By the housing portion housing the distal end portions of the larger number of built-in components, the need for walls between the built-in components is eliminated and the diameter of the distal end body is able to be reduced.

The disclosure enables provision of an endoscope and a distal end body that: enable reduction in diameter of the distal end body and two or more built-in components to be attached and detached individually one by one; and are not easily deteriorated over time.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An endoscope, comprising:
a distal end body that is positioned at a distal end of an insertion portion configured to be inserted into a subject; and
a first built-in component and a second built-in component each having a distal end portion housed in the distal end body, wherein
the distal end body comprises:
   a first housing portion that extends along a first direction along a longitudinal direction of the distal end body and houses the distal end portion of the first built-in component;
   a first opening portion in which the distal end portion of the first built-in component is fitted, the first opening portion communicating with the first housing portion and being open in at least a second direction;
   a second housing portion that communicates with the first housing portion, extends along the first direction at a position shifted in a third direction orthogonal to both the first direction and the second direction, and houses the distal end portion of the second built-in component; and
   a second opening portion in which the distal end portion of the second built-in component is fitted, the second opening portion communicating with the second housing portion and being open in at least the second direction,
wherein the second direction is a direction orthogonal to the first direction,
the distal end body is configured such that the distal end portion of the first built-in component, from a state where the distal end portion of the first built-in component is fitted into the first opening portion of the distal end body, configured to be slid in a first inserting direction having a component in the second direction to allow attachment and detachment relative to the distal end body and such that the distal end portion of the second built-in component, from a state where the distal end portion of the second built-in component is fitted into the second opening portion of the distal end body, configured to be slid in a second inserting direction having at least a component in the second direction to allow attachment and detachment relative to the distal end body; and
the first inserting direction excludes the first built-in component being slid only in the second direction and the second inserting direction excludes the second built-in component being slid only in the second direction.

2. The endoscope according to claim 1, wherein the first built-in component is an image sensor configured to capture an image of the subject by converting light received from outside of a distal end of the image sensor into an image signal.

3. The endoscope according to claim 1, wherein the second built-in component is a light source configured to emit illumination light to outside of a distal end of the light source.

4. The endoscope according to claim 1, wherein the first opening portion is formed on a distal end side of the distal end body with respect to the second opening portion and is separate from the second opening portion.

5. The endoscope according to claim 1, wherein a rear end of the first built-in component and a rear end of the second built-in component extend along the first direction at a same position along the third direction.

6. The endoscope according to claim 1, further comprising:
    a treatment tool raising stand configured to raise a treatment tool in the second direction, wherein
    the distal end body includes a treatment tool insertion channel where the treatment tool is to be inserted, the treatment tool insertion channel extending along the first direction.

7. The endoscope according to claim 1, wherein
    the first built-in component is an image sensor configured to capture an image of the subject by converting light received from outside of a distal end of the image sensor into an image signal,
    the second built-in component is a light source configured to emit illumination light to outside of a distal end of the light source, and
    the first opening portion is formed on a distal end side of the distal end body with respect to the second opening portion and is separate from the second opening portion.

8. The endoscope according to claim 7, wherein a rear end of the first built-in component and a rear end of the second built-in component extend along the first direction at a same position along the third direction.

9. The endoscope according to claim 7, further comprising:
    a treatment tool raising stand configured to raise a treatment tool in the second direction, wherein
    the distal end body includes a treatment tool insertion channel where the treatment tool is to be inserted, the treatment tool insertion channel extending along the first direction.

10. The endoscope according to claim 1, wherein the first built-in component and the second built-in component are individually detachable from the distal end body.

11. The endoscope according to claim 1, wherein a first cross-section and a second cross-section do not overlap each other, the first cross-section being a cross-section of an elliptical region where the first built-in component passes in a first plane orthogonal to the longitudinal direction when the first built-in component is attached or detached to or from the distal end body, the second cross-section being a cross-section of a circular region where the second built-in component passes in a second plane orthogonal the longitudinal direction when the second built-in component is attached or detached to or from the distal end body.

12. The endoscope according to claim 1, wherein the endoscope is an ultrasound endoscope including an ultrasonic observation device, and
    a feeding channel configured to feed liquid to a balloon and a suction channel configured to suction liquid from the balloon are located in the distal end body on a same side as an insertion channel in a direction orthogonal to a direction along the longitudinal direction with respect to a central axis of the distal end body, the insertion channel having a cable extending from the ultrasonic observation device.

13. The endoscope according to claim 1, wherein the first inserting direction and the second inserting direction are the same.

14. The endoscope according to claim 1, wherein the distal end body is configured such that the distal end portions of the first built-in component and the second built-in component are slid in a direction that further includes a component of the first direction to allow attachment and detachment relative to the distal end body.

15. A distal end body positioned at a distal end of an insertion portion of an endoscope configured to be inserted into a subject, the distal end body comprising:
    a first housing portion that extends along a first direction along a longitudinal direction of the distal end body and houses a distal end portion of a first built-in component;
    a first opening portion in which the distal end portion of the first built-in component is fitted, the first opening portion communicating with the first housing portion and be open in at least a second direction;
    a second housing portion that communicates with the first housing portion, extends along the first direction at a position shifted in a third direction orthogonal to both the first direction and the second direction, and houses a distal end portion of a second built-in component; and
    a second opening portion in which the distal end portion of the second built-in component is fitted, the second opening portion communicating with the second housing portion and be open in at least the second direction,
    wherein the second direction is a direction orthogonal to the first direction,
    the distal end body is configured such that the distal end portion of the first built-in component, from a state where the distal end portion of the first built-in component is fitted into the first opening portion of the distal end body, configured to be slid in a first inserting direction having a component in the second direction to allow attachment and detachment relative to the distal end body and such that the distal end portion of the second built-in component, from a state where the distal end portion of the second built-in component is fitted into the second opening portion of the distal end body, configured to be slid in a second inserting direction having at least a component in the second direction to allow attachment and detachment relative to the distal end body; and
    the first inserting direction excludes the first built-in component being slid only in the second direction and the second inserting direction excludes the second built-in component being slid only in the second direction.

16. The distal end body according to claim 15, wherein the first built-in component and the second built-in component are individually detachable from the distal end body.

17. The distal end body according to claim 15, wherein a first cross-section and a second cross-section do not overlap each other, the first cross-section being a cross-section of an elliptical region where the first built-in component passes in a first plane orthogonal to the longitudinal direction when the first built-in component is attached or detached to or from the distal end body, the second cross-section being a cross-section of a circular region where the second built-in component passes in a second plane orthogonal to the longitudinal direction when the second built-in component is attached or detached to or from the distal end body.

18. The distal end body according to claim 15, wherein the first inserting direction and the second inserting direction are the same.

19. The distal end body according to claim 15, wherein the distal end body is configured such that the distal end portions of the first built-in component and the second built-in component are slid in a direction that further includes a component of the first direction to allow attachment and detachment relative to the distal end body.

* * * * *